United States Patent
Tenerz

(12) United States Patent (10) Patent No.: US 7,263,894 B2
Tenerz (45) Date of Patent: Sep. 4, 2007

(54) SENSOR AND GUIDE WIRE ASSEMBLY

(75) Inventor: Lars Tenerz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 11/063,744

(22) Filed: Feb. 24, 2005

(65) Prior Publication Data

US 2005/0268724 A1 Dec. 8, 2005

Related U.S. Application Data

(60) Provisional application No. 60/577,197, filed on Jun. 7, 2004.

(51) Int. Cl.
*A61B 5/00* (2006.01)
*G01L 7/00* (2006.01)

(52) U.S. Cl. .......................... 73/756; 600/585

(58) Field of Classification Search ................ 257/676; 73/700, 721, 724; 338/4
See application file for complete search history.

(56) References Cited

U.S. PATENT DOCUMENTS

| | | | |
|---|---|---|---|
| 1,344,758 A | 6/1920 | Donnelly | |
| 4,463,336 A * | 7/1984 | Black et al. | .................. 338/4 |
| 5,029,479 A * | 7/1991 | Bryan | .......................... 73/721 |
| 5,132,658 A * | 7/1992 | Dauenhauer et al. | .......... 338/92 |
| RE35,648 E | 11/1997 | Tenerz et al. | |
| 6,112,598 A | 9/2000 | Tenerz et al. | |
| 6,167,763 B1 | 1/2001 | Tenerz et al. | |
| 6,182,513 B1 | 2/2001 | Stemme et al. | |
| 6,279,402 B1 * | 8/2001 | Fisher | .......................... 73/754 |
| 6,343,514 B1 | 2/2002 | Smith | |
| 6,461,301 B2 | 10/2002 | Smith | |
| 6,495,908 B2 * | 12/2002 | Yang et al. | ................. 257/676 |
| 6,615,067 B2 | 9/2003 | Hoek et al. | |
| 6,692,446 B2 | 2/2004 | Hoek | |
| 2003/0018273 A1 | 1/2003 | Corl et al. | |
| 2005/0000294 A1 | 1/2005 | Tenerz et al. | |
| 2005/0011272 A1 | 1/2005 | Tenerz | |
| 2005/0116729 A1 * | 6/2005 | Koester et al. | ............. 324/754 |

OTHER PUBLICATIONS

C. Li et al., "Polymer Flip-Chip Bonding of Pressure Sensors on Flexible Kapton Film for Neonatal Catheters," Proceedings of IEEE, Oct. 24-27, 2004, pp. 749-752.

F. Sauser et al., "Pressure Microsensing Catheters for Neonatal Care," Sensors, Proceedings of IEEE, Oct. 24-27, 2004; pp. 1476-1479.

* cited by examiner

*Primary Examiner*—Andre J. Allen
(74) *Attorney, Agent, or Firm*—Foley & Lardner LLP

(57) ABSTRACT

The invention relates to a sensor (23) adapted for a sensor and guide wire assembly for intravascular measurements in a living body, wherein the sensor (23) comprises a pressure sensitive part (24) and an electronic part (25), said pressure sensitive part (24) comprising a first chip (26) provided with at least one pressure sensitive device (27) and at least one piezoelectric element (35), and the electronic part (25) comprising a second chip (28) provided with at least one electric circuit, and wherein the pressure sensitive part (24) and electronic part (25) are spatially separated from each other and are electrically connected with at least one electrical lead (29).

10 Claims, 2 Drawing Sheets

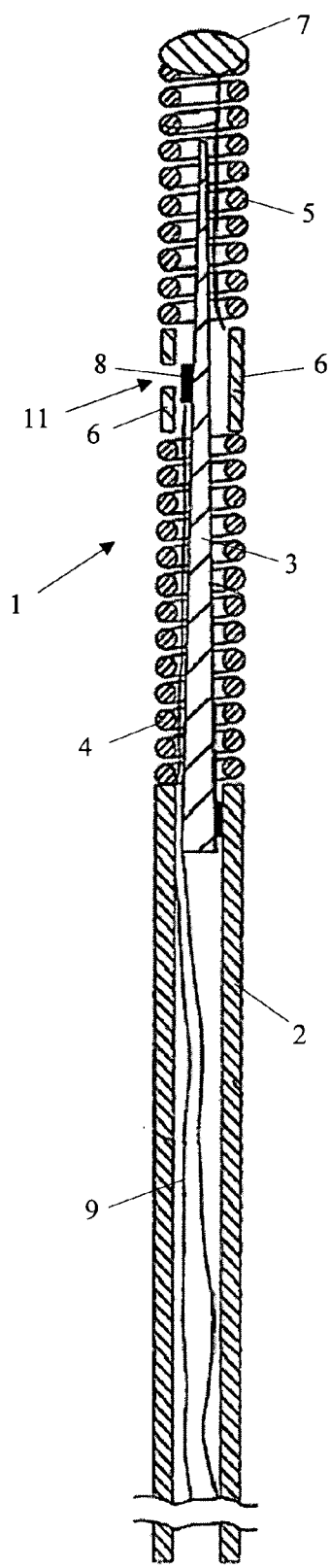
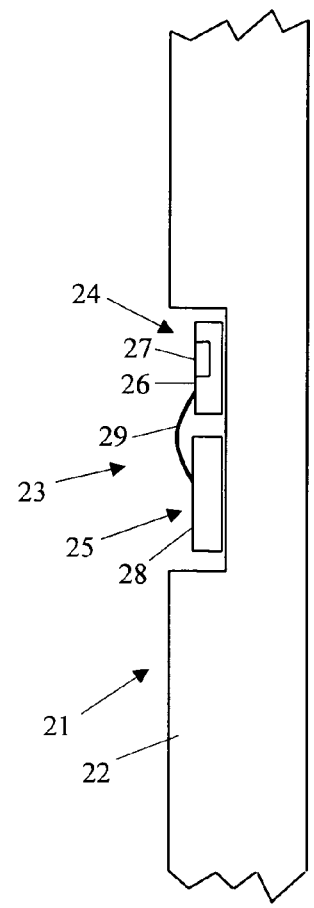
Fig. 1
(Prior Art)
Fig. 2

SENSOR AND GUIDE WIRE ASSEMBLY

FIELD OF THE INVENTION

The present invention relates generally to sensor and guide wire assemblies, in which a sensor is mounted at the distal end of a guide wire for intravascular measurements of physiological variables in a living body, and in particular to the design and arrangement of the sensor.

BACKGROUND OF THE INVENTION

Sensor and guide wire assemblies in which a sensor is mounted at the distal end of a guide wire are known. In U.S. Pat. No. Re. 35,648, which is assigned to the present assignee, an example of such a sensor and guide wire assembly is disclosed, where a sensor guide comprises a sensor element, an electronic unit, a signal transmitting cable connecting the sensor element to the electronic unit, a flexible tube having the cable and the sensor element disposed therein, a solid metal wire (also called a core wire), and a coil attached to the distal end of the solid wire. The sensor element comprises a pressure sensitive device, e.g. a membrane, with piezoresistive elements connected in a Wheatstone bridge-type of arrangement mounted thereon. An exemplifying electrical circuit arrangement can also be found in the present applicant's U.S. Pat. No. 6,343,514. As an alternative, the pressure sensitive device can also be in the form of a resonant structure, as is disclosed in the present applicant's U.S. Pat. Nos. 6,182,513 and 6,461,301. Instead of using cables to connect a sensor element to an electronic unit, other ways of receiving sensor signals can be employed. U.S. Pat. Nos. 6,615,067 and 6,692,446, which are assigned to the present assignee, disclose sensor systems for signal transmission via body tissues and passive biotelemetry, respectively.

As is recognized in U.S. Pat. Nos. 6,112,598 and 6,167,763, which also are assigned to the present assignee, a potential problem with this kind of guide wire mounted sensor is the occurrence of so-called bending artefacts. A bending artefact is a change in the output signal from the sensor that is induced by a bending of the guide wire, rather than being induced by a change in the physical environment surrounding the sensor. For a sensor and guide wire assembly like the one disclosed in Re. 35,648, this means that when the guide wire is bent, the bending of the guide wire imposes a strain on the sensor element, which thereby is deflected or stretched (or contracted). The deflection of the sensor element is then transferred to a deformation of the pressure sensitive device; and, according to well-known principles, the output from the Wheatstone bridge will thereby be affected by the bending of the guide wire.

According to U.S. Pat. Nos. 6,112,598 and 6,167,763, a solution to this problem is to mount the sensor element in a cantilevering fashion such that the pressure sensitive end of the sensor element does not contact any structure other than its mount. These two patents disclose several embodiments with different ways of mounting the sensor element such that bending forces are not exerted on the pressure sensitive end of the sensor element. A common feature of these embodiments is that an elongated, essentially rectangular sensor chip is mounted in a recess in the core wire in such a way that the proximal end of the chip is attached to the core wire, while the distal end of the sensor chip protrudes into the recess such that a clearance is provided below the distal portion of the chip where the pressure sensitive device (e.g. a membrane) is provided.

In the U.S. application Ser. No. 10/611,661, which is assigned to the present assignee, a principally different solution is presented. Here it is the design of the sensor element itself—rather than the mounting arrangement and design of the core wire—that provides the resistance against bending artefacts. According to Ser. No. 10/611,661, a sensor element comprises a mounting base, which provides for the desired cantilevered mounting of the sensor element.

In U.S. application Ser. No. 10/622,136, which is assigned to the present assignee, another design of a sensor element is disclosed, wherein the sensor element is provided with a recess that acts as a hinge or articulation, which constitutes a border between a first end portion and a second end portion of the sensor element. This recess prevents deformations of the second end portion from being transferred to the first end portion where the pressure sensitive device (e.g. a membrane) is arranged.

Although a sensor and guide wire assembly provided with a sensor chip designed and mounted according to the teachings of U.S. Pat. Nos. 6,112,598 and 6,167,763 in practise has proven to work well, the design of a sensor and guide wire assembly can be improved, not least from a manufacturing point of view.

SUMMARY OF THE INVENTION

As mentioned above, the sensor element according to the prior art comprises an elongated, essentially rectangular chip with a membrane made from polysilicon provided thereon. To achieve the desired resistance against bending artefacts, this chip can be designed and mounted in different ways. A common feature with the known designs is that the chip, including the pressure-sensitive membrane and the electric circuitry, is provided as one unit. The sensor element has thereby an elongated shape, with a length on the order of a millimeter. As already may have been appreciated from the discussion above, a shorter sensor chip would be less sensitive to bending artefacts. To simply reduce the chip length would, however, encounter several difficulties, not least in the manufacturing process.

An object of the present invention is to provide a new and improved design for a sensor arrangement so that, when the sensor is mounted in a sensor and guide wire assembly, the sensor and guide wire assembly will have the same or better characteristics regarding resistance against bending artefacts. Preferably, the sensor and guide wire assembly as well as the sensor chip should at the same time be easier and thereby cheaper to manufacture.

Another object of the invention is to provide a sensor design that facilitates the integration of more complex electronic circuitry in the sensor. With a more sophisticated electronic circuit, which, for example, includes components for signal conditioning and processing, improved signal characteristics and a more reliable sensor performance can be achieved.

A further object of the invention is to facilitate the incorporation of more delicate pressure sensitive devices, such as resonating structures, in the sensor.

These objects are achieved by a sensor arrangement and a sensor and guide wire assembly according to the independent claim(s). Preferred embodiments are set forth in the dependent claim(s).

A sensor and guide wire assembly comprises a sensor which, according to the prior art, is in the form of a generally rectangular and rather thin sensor chip with a pressure sensitive device provided thereon. The pressure sensitive device can be in the form of a membrane, which covers a small cavity in the upper side at a first end portion of the sensor chip and which has piezoresistive elements mounted thereon. According to the invention, this first portion is spatially separated from a second part of the sensor. A sensor thereby comprises a pressure sensitive part, which has a pressure sensitive device, such as a membrane, provided thereon, and at least one piezoresistive element mounted on the membrane. The second part of the sensor is also referred to as the electronic part, and includes, in a first embodiment of the invention, at least one electric circuit including at least one electric resistor and connection pads. In other embodiments of the invention, the electronic part can comprise a printed circuit with electronic logic and different signal processing elements. In a sensor and guide wire assembly, the first and second parts are spatially separated with, for example, a few millimeters and are electrically connected with at least one electric lead. The length of the pressure sensitive part—which is the part of a sensor that is potentially sensitive to bending artefacts—can thereby be reduced, which, in turn, makes it less sensitive to such bending artefacts. The length of the electronic part can, on the other hand, be increased, if this is desirable in order to incorporate more functionality in the electronic circuitry arranged thereon. Another advantage with physical division of the sensor in an electronic part and a pressure sensitive part is that these two parts easily can be manufactured by different techniques and even by different manufacturers. The two parts are then electrically connected during the assembly of the sensor and guide wire assembly.

BRIEF DESCRIPTION OF THE DRAWINGS

FIG. 1 illustrates the general design of a sensor and guide wire assembly according to the prior art.

FIG. 2 illustrates schematically a portion of a sensor and guide wire assembly comprising a sensor according to the present invention.

DETAILED DESCRIPTION OF THE INVENTION

Figure 3:
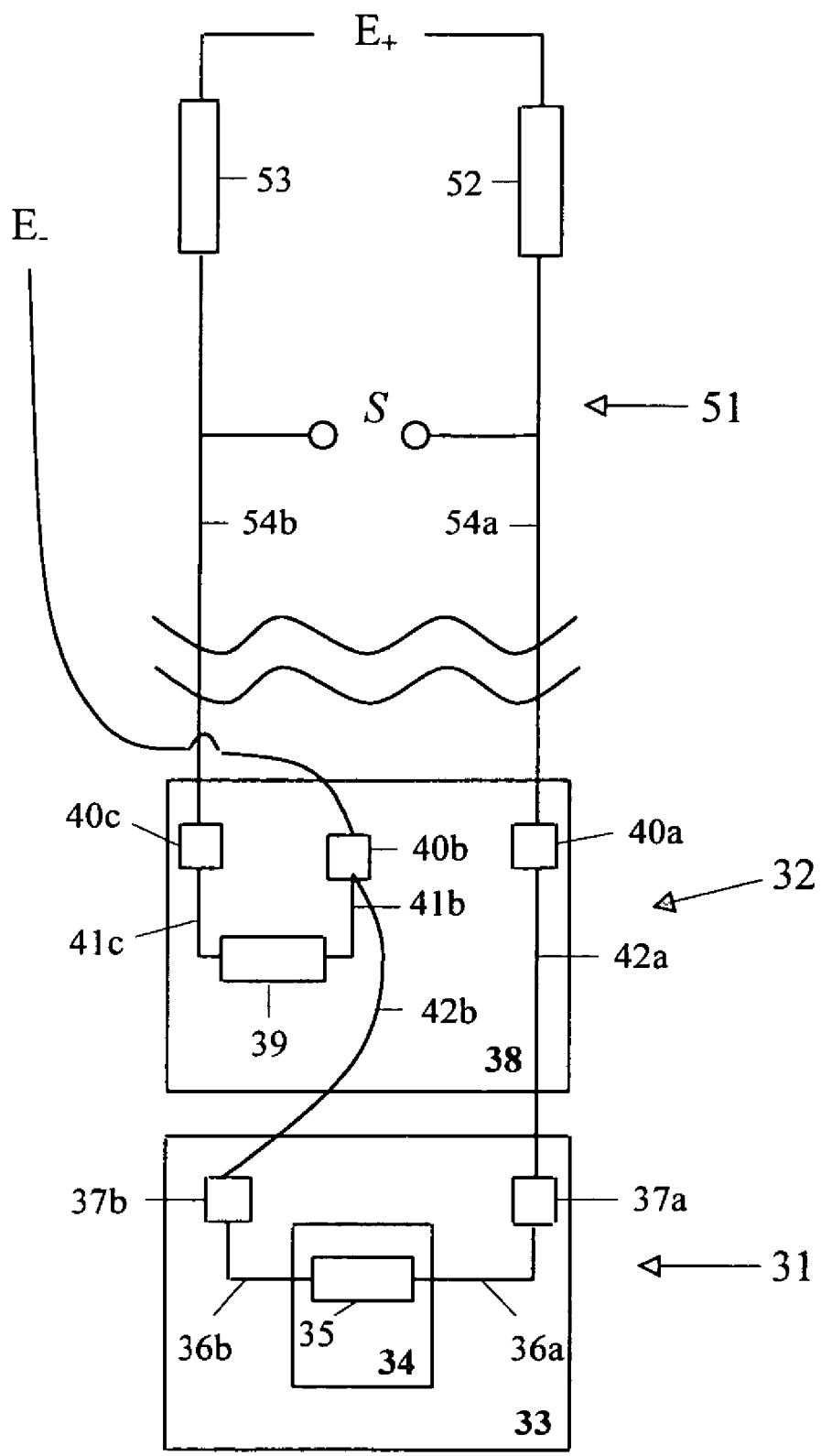
FIG. 3 illustrates an exemplifying coupling arrangement to be used together with a sensor according to the present invention.

For better understanding of the context in which a sensor according to the present invention is going to be used, a sensor and guide wire assembly 1 of a conventional design is illustrated in FIG. 1. The sensor guide 1 comprises a hollow tube 2, a core wire 3, a first coil 4, a second coil 5, a jacket or sleeve 6, a dome-shaped tip 7, a sensor element 8, and one or several electrical leads 9. The proximal end of the first coil 4 is attached to the distal end of the hollow tube 2, while the distal end of the first coil 4 is attached to the proximal end of the jacket 6. The proximal end of the second coil 5 is connected to the distal end of the jacket 6, and the dome-shaped tip 7 is attached to the distal end of the second coil 5. The core wire 3 is at least partly disposed inside the hollow tube 2 such that the distal portion of the core wire 3 extends out of the hollow tube 2 and into the second coil 5. The sensor element 8 is mounted on the core wire 3 at the position of the jacket 6, and is through the electrical leads 9 connected to an electronic unit (not shown in the figure). The sensor element 8 comprises a pressure sensitive device in the form of a membrane 10 (not visible in the figure), which through an aperture 11 in the jacket 6 is in contact with a medium, such as blood, surrounding the distal portion of the sensor guide 1. As is well known in the art, the dimensions as well as other properties of guide wires adapted for introduction into the artery can vary considerable based on the type of procedure being performed, the particular patient, etc. The corresponding ranges of dimensions are also applicable to a sensor guide whose distal end is provided with a sensor element. In one conventional design of a sensor guide like the sensor guide 1 shown in FIG. 1, the diameter of the tube 2 is about 0.014 inches (0.36 mm) and the dimensions of element 8 are 1340×180×100 µm (length× width×height).

Although not shown in the figure, the sensor element 8 further comprises an electrical circuitry, which in a Wheatstone bridge-type of arrangement is connected to one or several piezoresistive elements provided on the membrane 10. As is well known in the art, a certain pressure exerted on the membrane 10 from the surrounding medium will thereby correspond to a certain stretching or deflection of the membrane 10 and thereby to a certain resistance of the piezoresistive elements mounted thereon and, in turn, to a certain output from the sensor element 8. It should therefore be clear that it is highly preferable that this output from the sensor element 8 does not change due to factors that are not related to a real change in the physical properties of the surrounding medium. As was mentioned above, one such factor is so-called bending artefacts, the source of which is that a bending of the sensor guide 1 is transferred to a deformation of the membrane 10. Here, the discussion above about piezoresistive elements coupled in a Wheatstone bridge-type of arrangement should only be seen as an illustrative exemplification; in short, the basic problem is that a pressure sensitive device, such as a membrane, can be influenced by a bending of a sensor guide.

To remedy the potentially adverse effects from bending artefacts, the present invention provides a new design of a sensor to be used in a sensor and guide wire assembly. FIG. 2 shows schematically a portion of a sensor and guide wire assembly 21 comprising a core wire 22 and a sensor 23 according to the present invention. The sensor 23 comprises essentially two parts: a pressure sensitive part 24 and an electronic part 25. The pressure sensitive part 24 comprises a small chip 26, in which a cavity has been formed. The cavity is covered by a pressure sensitive device in the form of a membrane 27, on the surface of which at least one piezoresistive element is arranged (not shown in the figure). When the sensor 23 is used in a sensor and guide wire assembly, the pressure prevailing in the ambient medium will create a deflection of the membrane 27, which, in turn, changes the resistance of the piezoresistive element and accordingly the output of the sensor 23. The electronic part 25 includes at least one electric circuit, which is provided at the surface of a chip 28. The electronic part 25 is electrically connected to the pressure sensitive part 24 by at least one electric lead 29. An exemplifying coupling arrangement will be discussed in more detail in conjunction with the description of FIG. 3.

According to the invention, the electronic part 25 is disposed in the vicinity of the pressure sensitive part 24, and is electrically connected to the pressure sensitive part 24 with said at least one electrical lead 29. In this embodiment, the spatial separation between the pressure sensitive part 24 and the electronic part 25 is small, for example on the order of a few millimeters or even fractions of a millimeter, but also a larger spatial separation is conceivable. With the inventive division of the sensor 23 into a pressure sensitive part 24 and an electronic part 25, the pressure sensitive part 24 can be made very small since the number of electrical components, e.g. resistors, that have to be fitted onto the surface of the chip 26 is reduced in comparison with the known technical solutions. A smaller (shorter) pressure sensitive part is correspondingly less prone to bending artefacts, as has been outlined above. The length of the electronic part 25, which is insensitive, or at least comparatively insensitive, to bending artefacts, can, on the other hand, be increased to include more components, i.e. the components not provided in the pressure sensitive part 24, or further components to include more functionality in the sensor 23, or to provide the sensor 23 with better output characteristics. By dividing a sensor into one chip that comprises a pressure sensitive device and another chip that only contains elements that are pressure insensitive, the two chips can be manufactured by different methods and even by different manufacturers. The two chips are then mounted separately during the assembly of a sensor and guide wire assembly, and are electrically connected by at least one electrical lead.

An exemplifying coupling arrangement for a sensor according to the present invention is schematically illustrated in FIG. 3. This coupling arrangement is based on the previously discussed Wheatstone bridge-type of coupling; and for the sake of clarity, the number of electrical components provided at a pressure sensitive part 31 and an electronic part 32, respectively, has been minimized, but it should be understood that a much more sophisticated circuit solution can be implemented. This is in particular the case for the electronic part 32, whose size and thereby the available space for electrical components can be increased in accordance with an object of the invention.

As is seen from FIG. 3, the pressure sensitive part 31 comprises a chip 33, in which a cavity has been formed. The cavity is covered by a membrane 34, at the surface of which a piezoresistive element 35 has been provided. The piezoresistive element 35 is by a first electrical lead 36a connected to a first connection pad 37a, and by a second electrical lead 36b to a second connection pad 37b. The connection pads 37a, b are arranged at the surface of the chip 33 outside the membrane 34.

In this basic embodiment, the electronic part 32 comprises a chip 38, at the surface of which a resistor 39 and three connection pads 40a-c have been arranged. Two electrical leads 41b and 41c connect the resistor 39 to the connection pads 40b and 40c, respectively. The connection pad 40a is by an electrical lead 42a connected to the connection pad 37a at the pressure sensitive part 31, while an electrical lead 42b connects the connection pad 40b with the connection pad 37b. It should now be appreciated that the electrical circuit provided at the pressure sensitive part 31 and electronic part 32 forms one half of a Wheatstone bridge. For the sake of completeness, the other half of the Wheatstone bridge, which is generally referenced with reference number 51, has been illustrated in the upper portion of FIG. 3. This second or external half 51 of the Wheatstone bridge can be arranged within an external unit, such as a monitor, to which a sensor guide is connected and which also is used for numerically or graphically displaying information related to the sensor output.

The external half 51 of the Wheatstone bridge comprises a first resistance 52 and a second resistance 53. The first resistance 52 is by an electrical lead 54a connected to the connection pad 40a of the electronic part 32, while another electrical lead 54b connects the second resistance 53 to the connection pad 40c. A positive excitation voltage $E_+$ is applied over the resistances 52 and 53, while a negative excitation voltage E is applied directly to the connection pad 40b of the electronic part 32. A voltage difference S (i.e. a signal), which represents the resistance of the piezoresistive element 35 and thereby the pressure that the surrounding medium exerts on the membrane 34, can thereby be obtained between the electrical leads 54a and 54b.

It should, once again, be emphasized that the circuit arrangement described above is only an exemplifying arrangement. It is, for example, possible to provide a full Wheatstone bridge in a sensor according to the invention. In that case, the pressure sensitive part could comprise a piezoresistive element as described above, whereas the electronic part would include at least three resistors. In another arrangement, the pressure sensitive part could include also pressure insensitive resistors. A particular advantage with the present invention is the enhanced possibility to provide a more complex electrical circuit at an electronic part of a sensor. In that case, more sophisticated components, such as operational amplifiers, could be provided to improve the signal characteristics from the sensor. It is in particular possible that the electronic part comprises commercially available standard electronics, which, e.g., is provided as integrated circuits with the so-called CMOS technology. With a more sophisticated electrical circuit arrangement at the sensor side, the number of leads that connect a sensor to an external unit can be reduced, and even reduced to zero if a wireless signal transmission is employed. A wireless signal transmission is, for example, discussed in the above referenced patents. It is also possible to replace the piezoresistive element of the pressure sensitive part with another type of piezoelectrical component, for example a capacitive device which could be provided on the underside of a membrane and at the bottom of a recess, which is covered by that membrane, such that the capacitance of the capacitive device depends on the deflection of the membrane. The pressure sensitive device could also comprise a vibrating or resonating structure, whose vibration or resonance frequency is dependent on the pressure exerted by the ambient medium.

Although the present invention has been described with reference to a specific embodiment, also shown in the appended drawings, it will be apparent for those skilled in the art that many variations and modifications can be done within the scope of the invention as described in the specification and defined with reference to the claims below. It is, for example, possible to dispose an electronic part and a pressure sensitive part of a sensor in separate recesses in a core wire which is arranged inside a sensor and guide wire assembly. The invention can be used for intravascular measurements of other types of physiological variables such as temperature or flow, and is further applicable to direct as well as indirect measurements of such physiological variables. Also, features of the above-described embodiment may be combined with features of the U.S. patents and patent applications discussed in the background section above as well as with features of U.S. provisional applications 60/577,197 (filed Jun. 7, 2004 by Lars Tenerz and Sauli Tulkki) and 60/605,170 (filed Aug. 30, 2004 by Sauli Tulkki). The entire contents of all of these patents and applications are incorporated herein by reference.

What is claimed is:

1. A sensor adapted for a sensor and guide wire assembly for intravascular measurements in a living body, wherein the sensor comprises a pressure sensitive part and an electronic part;

said pressure sensitive part comprising a first chip provided with at least one pressure sensitive device and at least one element having at least one electrical property which varies with ambient pressure;

said electronic part comprising a second chip provided with at least one electric circuit;

the first chip and the second chip being spatially separated from each other and are electrically connected with at least one electrical lead.

2. A sensor according to claim 1, wherein the pressure sensitive device is a membrane that covers a recess provided in said first chip.

3. A sensor according to claim 1, wherein the pressure sensitive device comprises a vibrating structure.

4. A sensor according to claim 1, wherein the element is a piezoresistive element.

5. A sensor according to claim 1, wherein the element is a piezocapacitive element.

6. A sensor according to claim 1, wherein the electronic part comprises at least one integrated circuit.

7. A sensor and guide wire assembly being adapted for intravascular measurements in a living body and comprising a sensor, wherein the sensor comprises a pressure sensitive part and an electronic part;

said pressure sensitive part comprising a first chip provided with at least one pressure sensitive device and at least one element having at least one electrical property which varies with ambient pressure;

said electronic part comprising a second chip provided with at least one electric circuit;

the first part and the second chip being spatially separated from each other and are electrically connected with at least one electrical lead.

8. A sensor according to claim 1, wherein the first chip and the second chip are located side-by-side each other.

9. A sensor and guide wire assembly according to claim 7, further comprising a core wire for supporting the first and the second chip.

10. A sensor and guide wire assembly according to claim 7, wherein the first chip and the second chip are located side-by-side each other.

* * * * *